US006238680B1

(12) United States Patent
Picard et al.

(10) Patent No.: US 6,238,680 B1
(45) Date of Patent: May 29, 2001

(54) TWO-PHASE COSMETIC AND/OR DERMATOLOGICAL COMPOSITION WHICH CAN BE USED IN PARTICULAR FOR REMOVING MAKE-UP FROM THE EYES

(75) Inventors: Elisabeth Picard, Velizy; Lien Bui-Bertrand, Savigny sur Orge, both of (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/346,167

(22) Filed: Jul. 1, 1999

(30) Foreign Application Priority Data

Jul. 1, 1998 (FR) .................................................. 98 08416

(51) Int. Cl.⁷ ................................ A61K 6/00; A61K 7/00
(52) U.S. Cl. .......................... 424/401; 424/434; 424/400; 424/59
(58) Field of Search .................................. 424/400, 401, 424/434, 47, 59

(56) References Cited

U.S. PATENT DOCUMENTS 5,968,238  10/1999  Healy et al. ............................. 106/3

FOREIGN PATENT DOCUMENTS

| 33 40 350 A1 | 5/1985 | (DE) . |
| 0 116 422 A1 | 8/1984 | (EP) . |
| 0 370 856 A2 | 5/1990 | (EP) . |
| 0 446 094 A1 | 9/1991 | (EP) . |
| 0 603 080 A1 | 6/1994 | (EP) . |
| 2 645 740 | 10/1990 | (FR) . |

*Primary Examiner*—Dameron L. Jones
(74) *Attorney, Agent, or Firm*—Oblon, Spivak, McClelland, Maier & Neustadt, P.C.

(57) ABSTRACT

A cosmetic and/or dermatological composition containing an aqueous phase and a separate oily phase, containing, as a preserving agent, at least one ammonium bromide. Other preserving agents may be included in the composition. The composition is well-tolerated by the eyes and stores entirely satisfactorily, although it is in the form of two phases. It is used in particular for cleansing and/or removing make-up from the skin, mucous membranes and/or the eyes, and, most particularly, for removing make-up from sensitive eyes.

26 Claims, No Drawings

TWO-PHASE COSMETIC AND/OR DERMATOLOGICAL COMPOSITION WHICH CAN BE USED IN PARTICULAR FOR REMOVING MAKE-UP FROM THE EYES

BACKGROUND OF THE INVENTION

1. Field of the Invention

The present invention relates to a cosmetic and/or dermatological composition consisting of an aqueous phase and a separate oily phase, where the composition contains at least one ammonium bromide, and preferably myristyltrimethylammonium bromide, as a preserving agent. The present invention also relates to the use of this composition for cleansing and/or removing make-up from the skin, mucous membranes and/or the eyes, and in particular for removing make-up from sensitive eyes.

2. Description of the Background

It is known practice to use compositions which are in the form of two separate phases and which become emulsified by shaking and demix on standing, for removing make-up from the eyes. Such a composition is described in, for example, in EP-A-370,856.

These compositions in two-phase form contain preserving agents, in particular quaternary ammonium chlorides such as benzalkonium chloride. However, these compounds occasionally entail tolerance problems, in particular in individuals with sensitive eyes. As a result, it is an important goal to replace these preserving agents with agents which are better tolerated.

In addition, the preserving agents usually used in compositions in the form of a single phase are often relatively incompatible with the two-phase pharmaceutical form, since these conventional preserving agents lead to physicochemical instabilities giving rise to the formation of a film or a precipitate in the aqueous phase, or else they greatly disturb the water/oil interface leading to an undesirable appearance of the two-phase composition.

There is thus a need to have available a two-phase position which stores well, without having the drawbacks of known compositions, i.e., a composition which has both a pleasant appearance and good stability.

SUMMARY OF THE INVENTION

It is an object of the present invention to provide a composition having enhanced stability, where the composition has two phases: an aqueous phase and a separate oily phase.

It is another object of the present invention to provide methods of cleansing and/or removing make-up from the skin, mucous membranes and/or the eyes using the composition described above.

The present inventors have unexpectedly discovered that the use of at least one ammonium bromide, and in particular an alkyltrimethylammonium bromide, provides stable two-phase compositions with good properties of both physico-chemical and microbial storage, while at the same time allowing efficient make-up removal under highly satisfactory conditions of comfort and freshness. There was no indication that this preserving agent could be used successfully in two-phase compositions.

Accordingly, the objects of the present invention, and others, may be accomplished with a two-phase cosmetic and/or dermatological composition consisting of a separate aqueous phase and oily phase, where the composition also contains at least one ammonium bromide.

The objects of the invention may also be accomplished with a method of preserving a cosmetic composition comprising an aqueous phase and a separate oily phase, comprising incorporating an effective amount of an ammonium bromide, and in particular an alkyltrimethylammonium bromide into the composition.

The objects of the invention may also be accomplished with a method of cleansing and/or removing make-up from the skin, mucous membranes and/or the eyes, comprising applying the composition to the skin, mucous membranes and/or the eyes.

A more complete appreciation of the invention and many of the attendant advantages thereof will be readily obtained as the same becomes better understood by reference to the following detailed description.

DETAILED DESCRIPTION OF THE INVENTION

As ammonium bromides which can be used in the inventive composition alkyltrimethylammonium bromides are preferred. The alkyl radical of these compounds may contain from 1 to 22 carbon atoms and, more preferably, from 8 to 20 carbon atoms. These ranges include all specific values and subranges in between, including 2, 3, 5, 10, 12 and 18 carbon atoms.

Ammonium bromides which can be used in the composition, include, for example, dodecyltrimethylammonium bromide, myristyltrimethylammonium bromide and hexadecyltrimethylammonium bromide, and mixtures thereof. Myristyltrimethylammonium bromide is preferred.

It is possible, for example, to use myristyltrimethylammonium bromide (CTFA name: Mytrimonium bromide) either in its native state or in a mixture containing it, and in particular in a mixture with other ammonium bromides, for example in the mixture of dodecyltrimethylammonium bromide, myristyltrimethylammonium bromide and hexadecyltrimethylammonium bromide, sold under the name Cetrimide by FEF Chemicals.

The ammonium bromide is present in the composition of the invention in an amount which is sufficient to act as a preserving agent in the composition. Thus, this compound may be present in an amount ranging, for example, from 0.005 to 0.5% relative to the total weight of the composition, and preferably from 0.01 to 0.1% relative to the total weight of the composition. These weight % ranges include all specific values and subranges in between, such as 0.02, 0.05, 0.2, 0.3 and 0.4% by weight.

According to a preferred embodiment of the invention, the composition also contains, as an additional preserving agent, N-(3-chloroallyl)hexaminium chloride (CTFA name: quaternium-15), whose combination with a bromide is well tolerated and affords excellent preservative effect. The N-(3-chloroallyl)hexaminium chloride may be present in the composition of the invention in an amount ranging from 0 to 0.5% relative to the total weight of the composition, and preferably from 0.001 to 0.1% relative to the total weight of the composition. These ranges include all specific values and subranges therebetween, such as 0.002, 0.005, 0.01, 0.05, 0.2, 0.3 and 0.4% by weight.

The composition according to the invention comprises at least one aqueous phase (i.e., contains water) and a separate oily phase.

The aqueous phase in the composition of the invention may comprise sterile demineralized water and/or a floral water such as rose water, cornflower water, camomile water or lime water, or a thermal water or natural mineral water such as, for example: eau de Vittel, waters from the Vichy basin, eau d'Uriage, eau de la Roche Posay, eau de la Bourboule, eau d'Enghien-les-Bains, eau de Saint Gervais-les-Bains, eau de Neris-les-Bains, eau d'Allevar-les-Bains, eau de Digne, eau de Maizieres, eau de Neyrac-les-Bains, eau de Lons-le-Saunier, Eaux Bonnes, eau de Rochefort, eau de Saint Christau, eau des Fumades, eau de Tercis-les-bains and eau d'Avene. Mixtures of these waters may be used.

The oily phase in the composition according to the invention comprises at least one oil. The oil may be chosen from mineral, plant or synthetic oils or alternatively silicone oils, and mixtures thereof.

Among the mineral oils which may constitute the oily phase, preferable examples include liquid petroleum jelly and higher aliphatic hydrocarbons such as, for example, isohexadecane or isododecane; among the plant oils, jojoba oil and safflower oil; among the silicone oils, which may be volatile, cyclomethicones such as cyclopentadimethylsiloxane, and among the synthetic oils, alkyl palmitates in which the alkyl group contains from 2 to 10 carbon atoms, such as isopropyl palmitate or octyl palmitate, and alkyl adipates in which the alkyl group contains from 2 to 10 carbon atoms, such as bis(2-ethylhexyl) adipate, or any other aliphatic ester containing from 12 to 20 carbon atoms, and mixtures thereof.

According to one specific embodiment of the invention, the oily phase contains at least one oil chosen from alkyl palmitates, isohexadecane, isododecane, volatile silicone oils (cyclomethicones) and mixtures thereof.

When the composition contains an alkyl palmitate, the latter is preferably present in a proportion of at least 5% and better still in a proportion ranging from 8 to 30% of the total weight of the composition. These ranges include all specific values and subranges therebetween, such as 10, 12, 15, 20 and 25% by weight.

When the composition contains a volatile silicone oil, the proportion of this oil ranges, for example, from 5 to 50% of the total weight of the composition. These ranges include all specific values and subranges therebetween, such as 10, 15, 20, 25, 30 and 40% by weight.

In addition, the isohexadecane or the isododecane or a mixture of these two oils can be present in the composition of the invention in a proportion ranging from 5 to 20% relative to the total weight of the composition. These ranges include all specific values and subranges therebetween, such as 8, 10, 12, 15 and 18% by weight.

The two-phase composition according to the invention may be free of surfactant. However, it can also comprise at least one surfactant in one or other of the phases.

The surfactant is preferably anionic, nonionic or amphoteric. Preferably, the surfactant is nonionic. It is preferably present in the aqueous phase. The surfactant is preferably present in a proportion ranging from 0.01 to 10% (of active material) by weight relative to the total weight of the composition, and even more preferably from 0.025 to 3% of the total weight of the composition. These ranges include all specific values and subranges therebetween, such as 0.02, 0.05, 0.1, 0.2, 0.5, 1, 2, 5 and 8% by weight.

Among the nonionic surfactants, particularly preferred examples include:

polyoxyethylenated fatty esters of sorbitol, such as the product sold under the name Tween 20® by Atlas.

polyoxyethylenated fatty alcohols, such as the product sold under the name Remcopal 21912 AL® by Gerland.

polyoxyethylenated alkylphenols, such as the product sold under the name Triton X 100® by Rohm & Haas, and condensates of ethylene oxide and of propylene oxide (CTFA name: Poloxamer), such as those sold under the names Synperonic PE® by ICI and in particular those bearing the reference codes L 31, L 64, F 38, F 88, L 92, P 103, F 108 and F 127.

Among the anionic surfactants, preferable examples include:

alkyl ether sulphates, such as the product sold under the name Texapon ASV® by Henkel, alkyl sulphoacetates, such as the products sold under the name Lathanol LAL® by Stepan, alkyl sulphosuccinates, such as the product sold under the name Sodium dioctyl sulphosuccinate® by Rhône-Poulenc, alkylamido sulphosuccinates, such as the product sold under the name Rewoderm S 1333® by Rewo, alkylamido polypeptides, such as the product sold under the name Lamepon S® by Grunau, and acyl sarcosinates, such as the product sold under the name Oramix L 30® by Seppic.

Among the amphoteric surfactants, preferable examples include alkylamidopropyl dimethylbetaines, such as the product sold under the name Tego betaine L 7® by Goldschmidt, alkylamidobetaines, such as the product sold under the name Incronam 30® by Croda, imidazoline derivatives, such as the product sold under the name Chimexane HD® by Chimex, and N-alkyl-β-iminodipropionates, such as the product sold under the name Monateric ISA 35® by Mona.

The weight ratio between the aqueous phase and the oily phase preferably ranges from 30/70 to 60/40. This range includes all specific values and subranges therebetween, including 35/65, 40/60, 45/55, 50/50, and 55/45.

The composition of the invention suitably contains a physiologically acceptable medium, i.e., a medium which is compatible with the skin, mucous membranes and/or the hair.

In addition to the compounds indicated above, the composition according to the invention may also contain conventional cosmetic adjuvants, which will be found in one or other phase depending upon their hydrophilic or lipophilic nature, such as, for example, fragrances, dyes, softeners, a buffer, wetting agents, and optionally an electrolyte such as sodium chloride in order to make the aqueous phase isotonic, or any other suitable compound which is compatible with the two-phase composition of the invention.

Among the wetting agents, mention may be made in particular of glycerol, hexylene glycol and polyethylene glycol 600, these agents being present at a concentration of less than or equal to 5% and preferably ranging from 0.05 to 2% relative to the total weight of the composition. These ranges include all specific values and subranges therebetween, such as 0.01, 0.02, 0.1, 0.5, 1 and 3% by weight.

Among the softeners, mention may be made in particular of allantoin and certain plant extracts.

The compositions described above can be packaged, as is well-known, in a bottle with a single compartment. In this case, the user must shake the bottle before pouring some of the contents out onto a pad of cotton wool. It is also possible to envisage introducing the two phases of the composition into two separate compartments of the same bottle, with a system being provided for mixing them together at the time of dispensing. Such devices are described, for example, in EP-A-497,256 and FR-A-2,697,233, incorporated herein by reference.

Advantageously, the invention relates to care compositions and in particular to compositions for cleansing and/or removing make-up from the skin, mucous membranes such as the lips, and/or the eyes. It is particularly suitable for removing make-up from the eyes when the eyelashes carry mascara, in particular for removing make-up from sensitive eyes, and for removing make-up in the case of long-lasting and/or so-called "transfer-resistant" make-up compositions such as described, for example, in FR-A-2,747,566, incorporated herein by reference.

Thus, the invention also includes a process for cleansing and/or removing make-up from the skin, mucous membranes and/or the eyes, by applying the composition to the skin, mucous membranes and/or the eyes. The composition may, for example, be rubbed on to the area to be treated with the fingers. A specific embodiment is a process for removing make-up from sensitive eyes, characterized in that a composition as defined above is applied to the eyes.

Having generally described this invention, a further understanding can be obtained by reference to certain specific examples which are provided herein for purposes of illustration only and are not intended to be limiting unless otherwise specified.

EXAMPLES

In the composition described below, the percentages indicated are percentages by weight.

Example 1

| Two-phase composition | |
|---|---|
| Cyclomethicone | 28% |
| Isohexadecane | 19% |
| Myristyltrimethylammonium bromide | 0.005% |
| Poloxamer 184 (CTFA) | 0.04% |
| Phosphate buffer | 0.04% |
| Sodium chloride | 0.5% |
| Quaternium-15 | 0.03% |
| Dyes | qs |
| Demineralized water | qs 100% |

Obviously, additional modifications and variations of the present invention are possible in light of the above teachings. It is therefore to be understood that within the scope of the appended claims, the invention may be practiced otherwise than as specifically described herein.

This application is based on French Patent Application Serial No. 98-08416, filed on Jul. 1, 1998, and incorporated herein by reference in its entirety.

What is claimed is:

1. A two-phase composition comprising an aqueous phase, a separate oily phase, and about 0.005 to about 0.5% by weight of at least one ammonium bromide.

2. The composition of claim 1, wherein the ammonium bromide is an alkyltrimethylammonium bromide.

3. The composition of claim 1, wherein the ammonium bromide is selected from the group consisting of dodecyltrimethylammonium bromide, myristyltrimethylammonium bromide and hexadecyltrimethylammonium bromide, and mixtures thereof.

4. The composition of claim 1, wherein the ammonium bromide is myristyltrimethylammonium bromide.

5. The composition of claim 4, further comprising dodecyltrimethylammonium bromide and hexadecyltrimethylammonium bromide.

6. The composition of claim 1, comprising 0.005 to 0.5% by weight of the ammonium bromide.

7. The composition of claim 1, comprising 0.01 to 0.1% by weight of the ammonium bromide.

8. The composition of claim 1, further comprising N-(3-chloroallyl)hexaminium chloride.

9. The composition of claim 8, wherein comprising 0.001 to 0.1% by weight of the N-(3-chloroallyl)hexaminium chloride.

10. The composition of claim 1, wherein the oily phase contains at least one oil selected from the group consisting of silicone oils, higher aliphatic hydrocarbons, and synthetic oils.

11. The composition of claim 1, wherein the oily phase contains at least one oil selected from the group consisting of alkyl palmitates, isohexadecane, isododecane, volatile silicone oils, and mixtures thereof.

12. The composition of claim 1, further comprising at least one surfactant.

13. The composition of claim 12, which comprises 0.01 to 10% by weight of the surfactant.

14. The composition of claim 12, wherein the surfactant is anionic, nonionic or amphoteric.

15. The composition of claim 12, wherein the surfactant is selected from the group consisting of polyoxyethylenated fatty esters of sorbitol, polyoxyethylenated fatty alcohols, polyoxyethylenated alkylphenols, condensates of ethylene oxide or propylene oxide, alkyl ether sulphates, alkyl sulphoacetates, alkyl sulphosuccinates, alkylamido sulphosuccinates, alkylamido polypeptides, acyl sarcosinates, alkylamidopropyl dimethylbetaines, alkylamidobetaines, imidazolines, and N-alkyl-β-iminodipropionates.

16. The composition of claim 1, wherein the weight ratio of the aqueous phase and to oily phase is 30/70 to 60/40.

17. The composition of claim 1, which is suitable for topical application to human skin, mucous membranes, or eyes.

18. The composition of claim 1, further comprising at least one cosmetic adjuvant.

19. The composition of claim 18, wherein the cosmetic adjuvant is selected from the group consisting of fragrances, dyes, softeners, buffers, wetting agents, and electrolytes.

20. A method of preserving a cosmetic composition comprising an aqueous phase and a separate oily phase, comprising incorporating an effective amount of an ammonium bromide into the composition.

21. A method of cleansing and/or removing make-up from the skin, mucous membranes and/or the eyes, comprising applying the composition of claim 1 to the skin, mucous membranes and/or the eyes.

22. The method of claim 21, wherein the composition is applied to skin around the eyes.

23. A method of making the composition of claim 1, comprising combining the aqueous phase, oily phase and ammonium bromide.

24. A two-phase composition comprising an aqueous phase, a separate oily phase, and an ammonium bromide component comprising myristyltrimethylammonium bromide, dodecyltrimethylammonium bromide and hexadecyltrimethylammonium bromide.

25. A two-phase composition comprising an aqueous phase, a separate oily phase, and at least one ammonium bromide, and further comprising N-(3-chloroallyl) hexaminium chloride.

26. A method of cleansing and/or removing make-up from the skin around the eyes, comprising applying to skin around the eyes a two-phase composition comprising an aqueous phase, a separate oily phase, and at least one ammonium bromide.

* * * * *